United States Patent [19]

Gleason

[11] 3,934,591

[45] Jan. 27, 1976

[54] DERMATOME

[76] Inventor: Robert W. Gleason, 4608 Sharon Road, Camp springs, Md. 20031

[22] Filed: Mar. 20, 1974

[21] Appl. No.: 453,035

[52] U.S. Cl. .................. 128/305.5; 30/283; 30/329
[51] Int. Cl.² ........................................ A61B 17/322
[58] Field of Search ............. 30/121, 278, 283, 329; D32/40; 128/304, 305

[56] References Cited
UNITED STATES PATENTS

| 686,590 | 11/1901 | Council, Jr. | 30/121 |
| 1,627,901 | 5/1927 | Hills | 30/121 UX |
| 2,482,385 | 9/1949 | Urban et al. | 30/329 UX |

FOREIGN PATENTS OR APPLICATIONS

| 196,833 | 5/1923 | United Kingdom | 30/121 |
| 972,146 | 8/1950 | France | 128/304 |

Primary Examiner—Channing L. Pace
Attorney, Agent, or Firm—Strauch, Nolan, Neale, Nies & Kurz

[57] ABSTRACT

A dermatome having a handle and a replaceable, flexible cutting blade arranged over a T-shaped guide bar and support, both the blade and the support being adjustably secured to one end of the handle, providing an instrument for controlled, even depth removal of a graft from the donor site.

11 Claims, 7 Drawing Figures

U.S. Patent   Jan. 27, 1976   3,934,591
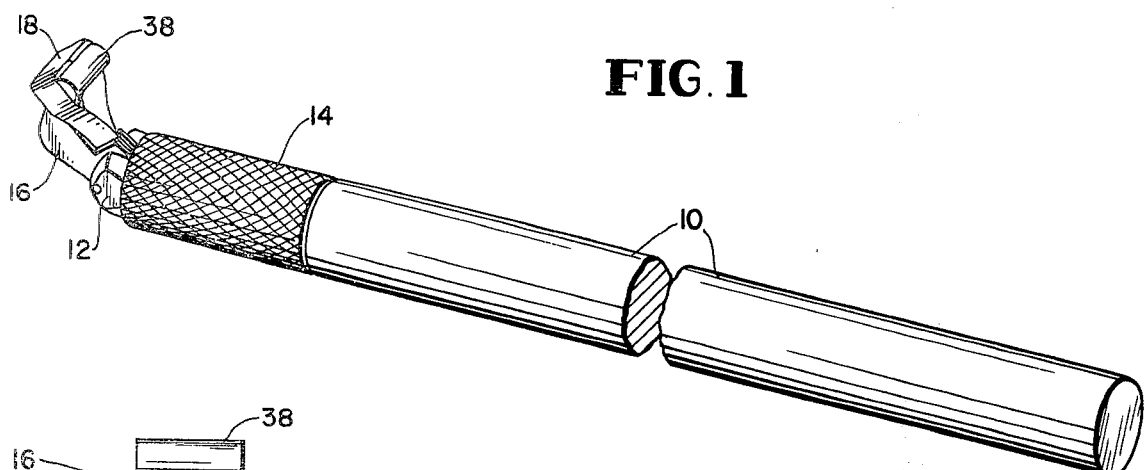
FIG. 1
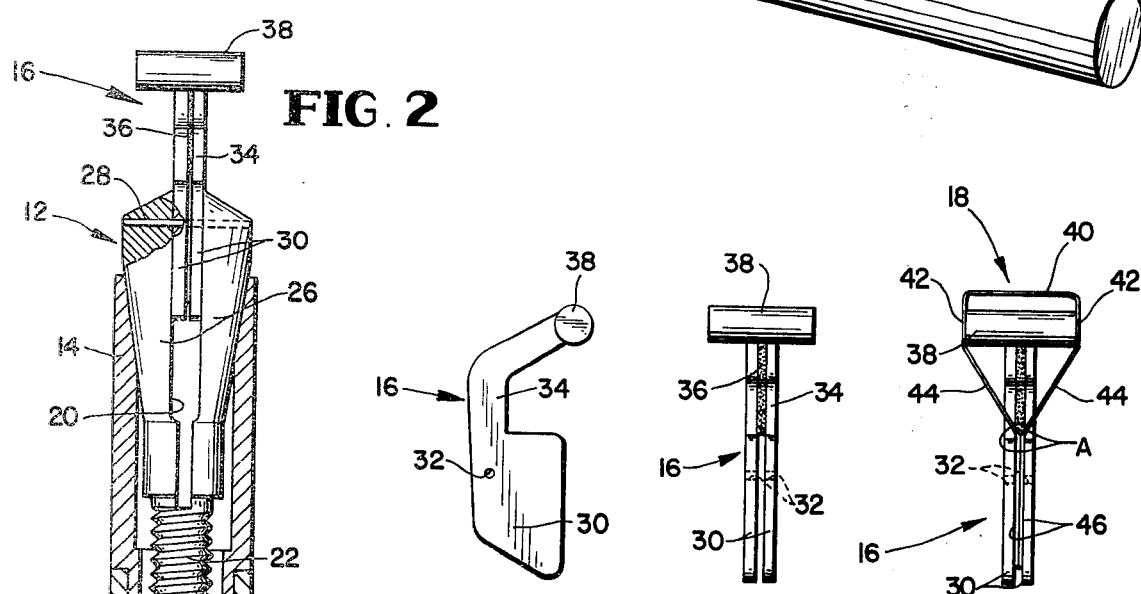
FIG. 2   FIG. 3   FIG. 4   FIG. 5
FIG. 6   FIG. 7

DERMATOME

BACKGROUND OF THE INVENTION

The field of the invention pertains to dermatomes generally, and in particular an improved dental surgery dermatome useful in the treatment of mucogingival defects involving inadequate attached gingiva. In such treatment, a graft or grafts of tissue are removed from the palate to increase the zone of attached gingiva.

In previously known practice, a scalpel was employed to make two elongate parallel cuts vertically through the epithelium, into the underlying connective tissue to delineate the long side boundaries of the graft, whereafter the graft would be removed starting with a horizontal incision at one end of the parallel cuts and removing a thin layer of palatal mucosa. This procedure provided a suitable graft but left the donor site with deep parallel wounds into the connective tissue which required healing before epithelial cells from the boundary areas could migrate over the wound. As a result, the healing process was unduly prolonged and, in most cases the patient would not be comfortable again until 2½ to 3 weeks elapsed after surgery.

More recently, a dermatome was developed including a bowed or unbowed blade, permanently or removably mounted at the end of a handle, the cutting edge of the blade being U-shaped or flat. Such blades are difficult to use in that the depth of the cut cannot be controlled other than by the experienced hand of the surgeon. Should the cut be too shallow, the graft will not take after implanting; if the cut is too deep, fatty tissue and glands will be removed which will have to be trimmed before grafting, and healing of the wound at the donor site will be even further prolonged. Furthermore, the blade tends to wobble, flex and undulate from side to side during the cut, due to lack of support for the blade, thereby leaving an uneven wound at the donor site and graft tissue that should be further trimmed prior to grafting. Additionally, the looped configuration of the blade produces a graft having shallow side edges that will slough off during healing or must be trimmed prior to grafting. In any event, even though such dermatomes represent a significant advance in the art, deficiencies remain as enumerated above which are overcome by the present invention.

The prior art includes several U. S. patents evidencing a development in similar surgical cutting instruments. Curettes having permanently mounted open or closed blades are disclosed in U. S. Pat. No's. 467,188; 872,567; and 2,521,161. Similar devices having removable blades are disclosed in U. S. Pat. No's. 3,013,553; 3,221,744 and 3,367,335. U. S. Pat. No. 3,502,082 issued to Chatfield discloses several varieties of a looped blade useful in dental surgery as discussed above, the looped blade assembly being disposable and replaced after use, but the blade is not adjustable to a suitable cutting angle with respect to the handle, as may be required when the donor site is located in a high vaulted palate. Adjustable non-looped blades useful in dental surgery are disclosed in U. S. Pat. No. 3,471,929, issued to Boone, but these blades are expensive to manufacture.

U. S. Pat. No. 3,688,407 issued to Omer E. Paquette discloses a looped blade dermatome now in use in dental surgery, the blade being replaceable and made by merely trimming an edge from a common stainless steel razor blade. Additionally, the blade may be secured at various cutting angles relative to the handle and the blade may be shaped to provide a bowed contour or it may be a flat, unbowed blade strip.

However, even in the case of the Paquette knife, depth control of the cut is not provided nor is side to side undulation of the knife prevented. Furthermore, no means are provided to assure that the present configuration of the blade (bowed or flat) will be retained during use.

SUMMARY OF THE INVENTION

Therefore, it is a principal object of the invention to provide a dermatome having a blade and blade support and cutting guide structure for removal of donor tissue of a predetermined depth.

It is another object of the invention to provide a dermatome having a handle with a blade and a combination cutting guide and blade support adjustable with respect to the handle to provide a variety of blade dispositions and facilitate blade replacement.

Yet another object of the invention is to provide a dermatome having a blade and blade support and cutting guide with locking means firmly securing the blade to the handle to prevent any shifting of the blade with respect to the handle during use.

A further object of the invention is to provide a dermatome with a blade and blade support and cutting guide structure whereby thickness of the graft may be preset to one of a variety of depths.

Still another object of the invention is to provide a dermatome having a blade and blade support and cutting guide structure for even, constant depth removal of the graft from the donor site to both shorten the time of the operation and promote rapid healing of the wound at the donor site.

Yet a further object of the invention is to provide a dermatome with a blade and blade support and cutting guide structure that removes a graft of evenly configured tissue, free of thin edges and of fat and glandular material.

It is still a further object of the invention to provide a dermatome having a blade and blade support and cutting guide structure both readily adjustable with respect to the handle without shifting the disposition of the blade on its support.

It is another object of the invention to provide a replaceable blade structure for a dermatome having a flat cutting edge and base support legs juxtaposed against one another in assembly in the dermatome whereby the blade is firmly secured in the dermatome and will not shift position in use.

Further novel features and other objects of this invention will become apparent from the following detailed description, discussion and the appended claims taken in conjunction with the accompanying drawings.

BRIEF DESCRIPTION OF DRAWINGS

A preferred structural embodiment of this invention is disclosed in the accompanying drawings in which:

FIG. 1 is a perspective view of the dermatome shown in complete assembly with the blade in position for removing a graft;

FIG. 2 is an enlarged scale, partially sectioned, front elevation view, of the dermatome shown in FIG. 1, the shaped blade being omitted for clarity of details;

FIG. 3 is a detail side elevation view of the blade support and cutting guide member shown in FIG. 2 of the dermatome;

FIG. 4 is a front elevation view of the dermatome blade support and cutting guide member shown in FIG. 3;

FIG. 5 is a view showing the blade support and cutting guide member of FIG. 4 with a blade disposed in position on the blade support;

FIG. 6 is a detail view of the blade support in assembly with the collet which is mounted in the dermatome handle as shown in FIG. 2 and further showing alternative dispositions in phantom lines; and FIG. 7 is a side elevation of the blade and blade support and cutting guide as shown in FIG. 5.

DESCRIPTION OF THE PREFERRED EMBODIMENTS

A dermatome is shown in the drawings including a handle 10, blade mounting collet chuck assembly 12 and its sleeve 14, a blade support and cutting guide 16 and blade 18. The handle 10, collet 12 and sleeve 14 are standard components of the well known X-acto brand razor knife. When used as intended by X-acto, collet 12 is split centrally at 20 to receive a razor knife (not shown) which is assembled onto handle 10 by grasping sleeve 14 while rotating handle 10 to thread the threaded base 22 of collet 12 into a matingly threaded bore 24 of handle 10. This action compresses wedge arms 26 of collet 12 together as collet 12 is drawn into sleeve 14 thereby firmly locking a razor knife normally disposed therebetween (not shown).

For use in this invention, the split at 20 is enlarged to receive the lower end of blade support and cutting guide 16 and collet wedge arms 26 are transversely bored at the upper end to receive a mounting pin 28 for pivotally securing blade support and cutting guide 16 between wedge arms 26. Blade support and cutting guide 16 includes lower, compressible base wings 30, bored at 32 to receive the pin 28, stem member 34, formed as flat extensions of wings 30 and silver soldered together at 36, and crossbar 38, soldered centrally thereof to the top of stem member 34. The crossbar can be made with a laterally curved contour, if desired.

Thus blade support and cutting guide 16 forms a T-bar blade support assembly, as best seen in FIGS. 2 and 4. Blade 18 may be made from one side of a commonly available stainless steel razor blade, bent to form a relatively flat, mesial cutting portion 40, side walls 42 against crossbar 38, angled support legs 44 disposed against the forward edge of stem 34, and base legs 46 compressed together and inserted into the space between wings 30 of blade support 16 (FIG. 5).

When the dermatome is assembled, as shown in FIG. 1, blade 16 is securely locked at two points to prevent any shifting of blade 16 with respect to the remaining parts of the dermatome, because blade base legs 46 are firmly wedged between wings 30 as wedge arms 26 are withdrawn into sleeve 14 in assembling the X-acto handle as previously described (FIG. 1), and because blade angled legs 44 are forced against stem 34 (FIG. 7) at locations A during a cutting operation, which is to the right in the sense of FIGS. 1 and 7. During cutting, blade 18 is prevented from wobbling from side to side due to the firm lateral support provide by crossbar 38 bearing against side walls 42 of blade 18.

To assemble a blade in the structure, parts are loosened by grasping sleeve 14 and unthreading collet 12 from handle 10 a sufficient distance so that wings 30 pivot upwardly and clear of sleeve 14. This disposition is shown by phantom lines in FIG. 6, with crossbar 38 at the left. A blade 18 is placed upon support and cutting guide 16 so that base legs 46 are located between wings 30, angled legs 44 rest against the face of stem 34, at location A, and side walls 42 are disposed adjacent either end of crossbar 38 (FIG. 7). The separation distance between cutting portion 40 of blade 18 and crossbar 38 may be preset by means of a thickness gauge or shim inserted between these members (not shown). Blade 18 and its support and cutting guide 16 are then rotated to one of a variety of cutting positions such as shown in solid lines in FIG. 6, or to the right, shown by phantom lines in FIG. 6. The handle assembly is then tightened as previously described and the shim (not shown) is removed. FIG. 1 illustrates one preferred disposition of parts, with blade 18 arranged at a rake angle to remove a tissue graft.

As the cutting proceeds, crossbar 38 provides a steady, fixed guide against the outer surface of the graft being removed so that an even depth of tissue is removed from the donor site. The distance between blade cutting portion 40 and crossbar guide 38 (FIG. 5) may be finely adjusted to as shallow a depth as ½ mm to remove a thin graft, if desired. Thus, a thin tissue graft may be removed with epithelial remnants scattered at the donor site to aid in the healing process. Of course, the disposition of blade cutting portion 40 and crossbar guide 38 may be adjusted for thicker grafts, if the surgeon so desires.

Experience has shown that healing time with thin grafts is drastically reduced at the wound in the donor site, to a period of from only 1½ to 2 weeks. The provision of blade adjustability permits a contra angle disposition of parts as shown in FIG. 1 so that even a donor site located in a high vaulted palate may be easily reached with the dermatome. Because of the rapid healing provided by use of the disclosed dermatome, up to 100 mm in length of tissue may be grafted during a single operation. Because of the even depth of cutting provided, it is unlikely that underlying fat and glandular material will be removed with the graft.

In the preferred embodiment shown, cutting portion 40 of blade 18 is approximately 5 mm long and all parts are made from stainless steel so that the entire instrument may be sterilized by autoclaving after use.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A dermatome comprising: a handle, a gripping device in the handle; blade support and cutting guide means; and cutting blade means mounted in the gripping device; said blade means comprising a generally elongate, flexible blade having a central, cutting portion and flat end portions bent from said central portion into juxtaposed, face to face abutting relationship, and said blade support and cutting guide means comprising a lateral support portion disposed beneath and generally coextensive with the long dimension of said blade central cutting portion and a base portion having means for mounting said blade flat end portions, said base portion being engaged and clamped by said gripping device, said lateral portion comprising a support, said blade central cutting portion being mounted on and over said support in predetermined spaced relationship thereto.

2. The dermatome as recited in claim 1 wherein said gripping device comprises a collet chuck assembly having a collet and a sleeve about said collet, said collet comprising a threaded base member, received in a matingly threaded bore in said handle, a pair of wedge shaped jaws at the upper end of the collet engaging and clamping said base portion therebetween, means defining aligned bores through said jaws, and pin means in said bores and through said base portion for pivotally mounting said blade support and cutting guide means between said jaws whereby said blade support and cutting guide means and said cutting blade means may be predisposed in any one of a variety of angular relationships with respect to said handle, in assembly.

3. The dermatome as recited in claim 1 wherein said blade end portion mounting means comprise a pair of coplanar, flat wing members having planar dimensions at least coextensive with the dimensions of said blade end portions, said blade end portions being located between said wing members and juxtaposed together therein.

4. The dermatome as recited in claim 1 wherein said base portion support further comprises a blade abutment portion between said blade end portion mounting means and said lateral portion for abutting relationship with intermediate portions of said cutting blade means located between said central, cutting portion and said blade end portions whereby, during a cutting operation, said cutting blade means are firmly secured both by said gripping means and by engagement between said stem blade abutment portion and said blade intermediate portions.

5. The dermatome as recited in claim 1 wherein the ends of said lateral portion engage side portions of said blade, bent thereover whereby said blade central cutting portion is firmly supported closely adjacent its end portions and said cutting guide controls the depth of a cut by contact with the face of tissue being cut during a cutting operation.

6. The dermatome as recited in claim 1 wherein said blade support and cutting guide means comprises a T-shaped support having a stem and a crossbar.

7. The dermatome as recited in claim 6 wherein said crossbar comprises a generally cylindrical bar mounted centrally thereof on top of said support stem.

8. The dermatome as recited in claim 6 wherein said blade central cutting portion has a length of approximately 5 mm.

9. A unitary, one piece cutting blade structure for use in a dermatome or the like comprising a generally elongate, flexible blade having a central, flat, tissue cutting portion, means defining a tissue cutting edge on at least one long edge of said central cutting portion, flat end portions bent from said central portion into juxtaposed, face to face abutting relationship and located centrally adjacent one side of said blade central portion and being disposed at approximately a 90° angle thereto, and intermediate blade portions formed in said elongate, flexible blade between the ends of said central cutting portion and said flat end portions, each of said intermediate blade portions comprising a first support portion, bent from an end of said central portion at approximately a 90° angle thereto, and a second support portion, bent from an end of said first support portion to an end of a respective flat end portion.

10. For use in a dermatome, the subcombination of a collet, a cutting guide and blade support member and a cutting blade means adapted as a unit assembly to be clamped together in a dermatome handle assembly, said cutting blade means comprising a generally elongate, flexible blade having a central cutting portion and portions bent from adjacent each end of said central portion terminating in flat end portions in juxtaposed, face to face abutting relationship, said cutting guide and support member comprising a lateral support portion inserted between said blade bent portions, beneath said central portion and a base portion having blade end portion mounting means in the stem thereof, said collet comprising a base member adapted to be secured in the said handle, a pair of wedge shaped jaws at the upper end of the collet embracing said base portion therebetween, means defining aligned bores through said jaws, and means in said bores and through said base portion for pivotally mounting said cutting guide and support member between said jaws whereby said guide and support member and said cutting blade means may be predisposed in any one of a variety of angular relationships with respect to said collet prior to clamping together of said unit assembly in said dermatome handle assembly.

11. The subcombination unit assembly as defined in claim 10, wherein said blade end portion mounting means support comprise a pair of coplanar, flat wing members having planar dimensions at least coextensive with the dimensions of said blade end portions, said juxtaposed blade end portions being disposed between said wing members, said base portion further comprising a blade abutment portion between said blade end portion mounting means and said lateral support portion for abutting relationship with intermediate portions of said cutting blade means located between said central portion and said blade end portions.

* * * * *